United States Patent
Jana et al.

(10) Patent No.: US 12,054,446 B2
(45) Date of Patent: Aug. 6, 2024

(54) METHOD FOR AROMATIZATION OF LOWER HYDROCARBONS TO PRODUCE BENZENE AND OTHER AROMATICS

(71) Applicant: SABIC GLOBAL TECHNOLOGIES B.V., Bergen op Zoom (NL)

(72) Inventors: Suman Kumar Jana, Bangalore (IN); Ninad Loke, Bangalore (IN); Selvakumar Subramanian, Bangalore (IN); Amit Kumar, Bangalore (IN); SreenivasaRao Gajula, Bangalore (IN)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 190 days.

(21) Appl. No.: 17/776,303

(22) PCT Filed: Nov. 10, 2020

(86) PCT No.: PCT/IB2020/060586
§ 371 (c)(1),
(2) Date: May 12, 2022

(87) PCT Pub. No.: WO2021/094926
PCT Pub. Date: May 20, 2021

(65) Prior Publication Data
US 2022/0396535 A1 Dec. 15, 2022

Related U.S. Application Data

(60) Provisional application No. 62/934,625, filed on Nov. 13, 2019, provisional application No. 62/934,624, filed on Nov. 13, 2019.

(51) Int. Cl.
*C07C 2/76* (2006.01)

(52) U.S. Cl.
CPC ............ *C07C 2/76* (2013.01); *C07C 2523/42* (2013.01); *C07C 2523/62* (2013.01); *C07C 2529/44* (2013.01)

(58) Field of Classification Search
CPC ... C07C 2/76; C07C 2523/42; C07C 2523/62; C07C 2529/44; C07C 2523/63;
(Continued)

(56) References Cited

U.S. PATENT DOCUMENTS

| 9,144,790 B2 | 9/2015 | Lauritzen et al. |
| 2002/0072642 A1 | 6/2002 | Allison et al. |

(Continued)

FOREIGN PATENT DOCUMENTS

| DE | 256513 A1 | 5/1988 |
| EP | 0186949 A1 | 7/1986 |

(Continued)

OTHER PUBLICATIONS

Chinese Office Action for the corresponding Chinese Application No. 202080077045.2; Date of Mailing: Aug. 23, 2023; 9 pages. (English translation unavailable).

(Continued)

*Primary Examiner* — Ali Z Fadhel
(74) *Attorney, Agent, or Firm* — CANTOR COLBURN LLP

(57) ABSTRACT

A method for the aromatization of hydrocarbons, comprising: introducing a feed stream to an aromatization catalyst in a fixed bed reactor wherein the feed stream comprises a hydrocarbon having 2 to 4 carbon atoms, converting the hydrocarbon having 2 to 4 carbon atoms to form an outlet stream comprising an aromatic hydrocarbon; wherein the feed stream is introduced at a GHSV of greater than or equal to 4,000 milliliters per gram of catalyst per hour (ml·g$^{-1}$ Cat·h$^{-1}$), and a pressure of greater than or equal to 0.4 MPa.

(Continued)

The feed stream can comprise hydrogen in an amount of at least 0.1 volume percent (vol %) up to 20 vol % based upon total volume of the feed stream.

20 Claims, 7 Drawing Sheets

(58) Field of Classification Search
CPC .............. C10G 2400/30; C10G 50/00; C10G 2300/1081; Y02P 20/141
See application file for complete search history.

(56) References Cited

U.S. PATENT DOCUMENTS

| | | |
|---|---|---|
| 2011/0130606 A1 | 6/2011 | Kiesslich et al. |
| 2012/0022310 A1 | 1/2012 | Schneider et al. |
| 2012/0253089 A1* | 10/2012 | Iyer .................... C07C 2/76 585/300 |
| 2013/0131414 A1 | 5/2013 | Iyer et al. |
| 2013/0338415 A1 | 12/2013 | Iyer et al. |
| 2016/0176779 A1 | 6/2016 | Zubrin et al. |
| 2016/0237002 A1 | 8/2016 | Vestre et al. |
| 2016/0251279 A1 | 9/2016 | Tanev et al. |
| 2016/0251280 A1 | 9/2016 | Tanev et al. |
| 2018/0370870 A1 | 12/2018 | Knaeble |

FOREIGN PATENT DOCUMENTS

| | | |
|---|---|---|
| WO | 2017136490 A1 | 8/2017 |
| WO | 2018111955 A1 | 6/2018 |

OTHER PUBLICATIONS

Harris, J. L. et al., "Aromatization of propane over a zeolite catalyst in both a microreactor and pilot plant" Applied Catalysis A: General, vol. 83, 1992; pp. 59-74.
International Search Report mailed Feb. 15, 2021; International Application No. PCT/IB2020/060586; International Filing Date Nov. 10, 2020 (6 pgs.).
Steinberg, K-H. et al., Aromatization of ethane on platinum containing ZSM-5 zeolites, Applied Catalysis, vol. 66, 1990; pp. 37-44.
Matsuoka, et al., "Effects of Ga content and reaction pressure upon the aromatization of propane over H—Ga—Al-pimetallosilicate catalysts," J Porous Mater, vol. 20, 2013; pp. 367-373.
Samanta, A. et al., "Conversion of Light Alkane to Value-Added Chemicals over ZSM-5/Metal Promoted Catalysts," Industrial & Engineering Chemistry Research, vol. 56, 2017; pp. 11006-11012.
Written Opinion mailed Feb. 15, 2021; International Application No. PCT/IB2020/060586; International Filing Date Nov. 10, 2020 (9 pgs.).
Xiang, Y. et al., "Progress and Prospects in Catalytic Ethane Aromatization," Catalysis Science & Technology, vol. 8, 2018; pp. 1500-1516.

\* cited by examiner

METHOD FOR AROMATIZATION OF LOWER HYDROCARBONS TO PRODUCE BENZENE AND OTHER AROMATICS

CROSS-REFERENCE TO RELATED APPLICATIONS

This application is a National Stage application of PCT/IB2020/060586, filed Nov. 10, 2020, which claims benefit of U.S. Application No. 62/934,624 filed on Nov. 13, 2019 and U.S. Application No. 62/934,625 filed on Nov. 13, 2019, all of which are incorporated by reference herein in their entirety.

BACKGROUND

Aromatic compounds such as benzene, toluene, and xylene can be made by aromatization of lower hydrocarbons, such as ethane, propane and butane. This can occur by contacting the lower hydrocarbon or hydrocarbons with an aromatization catalyst. Hydrogen gas is a by-product of the reaction. More moles of hydrogen gas are produced than there are molecules of gas consumed.

It is desired to process more of the lower hydrocarbon per gram of catalyst, to improve aromatics productivity, while maintaining catalyst long-term performance and stability.

BRIEF DESCRIPTION

Disclosed herein is a method for the aromatization of a lower hydrocarbons (e.g. having 2 to 4 carbon atoms), comprising: introducing a feed stream to an aromatization catalyst in a fixed bed catalyst reactor wherein the feed stream comprises a hydrocarbon having 2 to 4 carbon atoms; converting the hydrocarbon having 2 to 4 carbon atoms to form an outlet stream comprising an aromatic hydrocarbon; wherein the feed stream is introduced at a gas hourly space velocity (GHSV) of greater than or equal to 4,000 milliliters per gram of catalyst per hour (ml·(g of Cat)$^{-1}$·h$^{-1}$), and a pressure of greater than or equal to 0.4 megaPascals (MPa). The feed stream can further comprise hydrogen in an amount of from 0.1 to 29 volume percent (vol %) based on total volume of the feed stream.

The above described and other features are exemplified by the following figures and detailed description.

BRIEF DESCRIPTION OF THE DRAWINGS

The following figures are exemplary embodiments wherein the like elements are numbered alike.

DETAILED DESCRIPTION

Figure 1A:
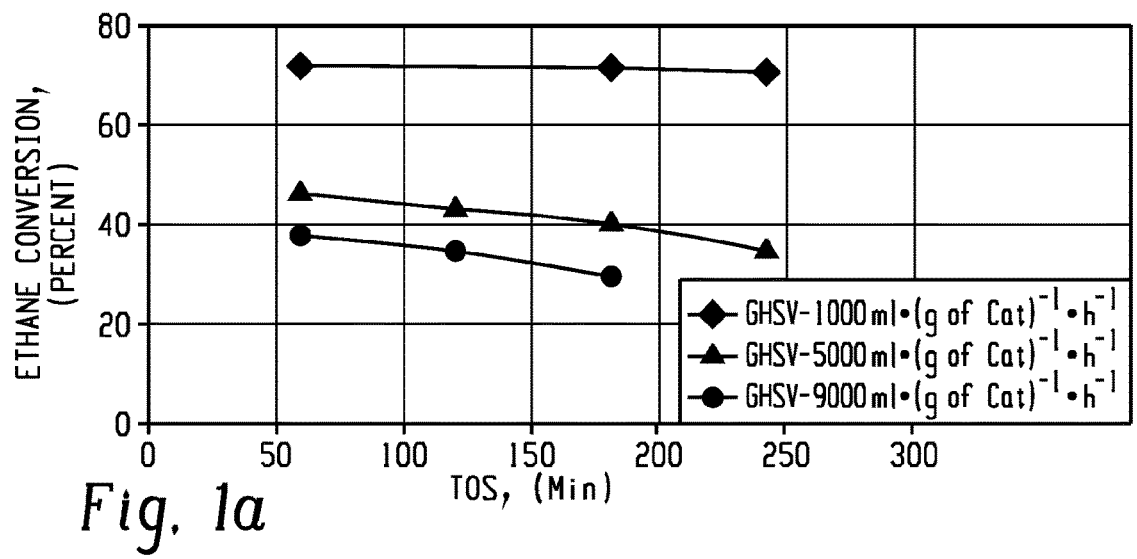
FIG. 1a-1c are graphical representations of ethane conversion, benzene productivity and benzene/toluene/xylene (BTX) productivity for a variety of GHSV at 5 bar (0.5 MPa) pressure.

While various references, (see e.g. US US2016/0251279, US2016/0176779, US2012/0253089, US2013/0338415, US2013/0131414, EP186949, US2016/0237002) teach aromatization of certain hydrocarbons at a range of pressure and gas flow rates, they generally prefer and/or exemplify relatively low pressures. Since hydrogen gas is a by-product of the aromatization reaction of lower alkyls and more moles of hydrogen gas are produced than are consumed, the reaction is favored at low pressure as is explicitly indicated in WO2018/111955. In addition, it has been recognized that "addition of $H_2$ is not suitable for light alkane aromatization since the increase of $H_2$ partial pressure both inhibits alkane dehydrogenation (a critical step for aromatization of alkanes) and increases the rate of the undesired hydrogenolysis reaction (forming $CH_4$)." Xiang et al. "Progress and prospects in catalytic ethane aromatization", Catal. Sci. Technol., 2018, vol. 8, 1500, 1510.

Surprisingly, as disclosed herein, use of pressure of greater than 0.4 MPa with gas hourly space velocities of at least 4000 ml·(g of Cat)$^{-1}$·h$^{-1}$, can lead to comparable ethane conversion to reactions occurring at lower pressures and lower gas flow rates while attaining higher aromatics productivity. In addition, surprisingly, addition of small amounts of hydrogen (e.g. 0.1 to 20 vol %, or 0.1 to 15 vol %, or 0.1 to 10 vol %, or 0.1 to 8 vol %, or 0.1 to 5 vol %, or 0.1 to 3 vol %, or 0.5 to 20 vol %, or 0.5 to 15 vol %, or 0.5 to 10 vol %, or 0.5 to 8 vol %, or 0.5 to 5 vol %, or 0.5 to 3 vol %, or 1 to 20 vol %, or 1 to 15 vol %, 1 to 10 vol %, or 1 to 8 vol %, or 1 to 5 vol %, or 1 to 3 vol %) in the feed stream can lead to improved long-term catalyst performance without substantial decrease of initial catalyst performance.

The method disclosed herein for the aromatization of hydrocarbons having 2 to 4 carbon atoms, comprises: introducing a feed stream to an aromatization catalyst in a fixed bed catalyst reactor wherein the feed stream comprises a hydrocarbon having 2 to 4 carbon atoms; converting the hydrocarbon having 2 to 4 carbon atoms to form an outlet stream comprising an aromatic hydrocarbon; wherein the feed stream is introduced at a gas hourly space velocity (GHSV) of greater than or equal to 4,000 milliliters per gram of catalyst per hour ("ml·(g of Cat)$^{-1}$·h$^{-1}$"), and a pressure of greater than or equal to 0.4 MPa. The feed stream can further comprise hydrogen in an amount of from 0.1 to 29 volume percent (vol %) based on total volume of the feed stream.

The ethane conversion can be at least 30% or at least 40% or at least 45% or at least 50% at less than 50 minutes time on stream and can be at least 10, or at least 12, or at least 15, or at least 18, or at least 20, or at least 30% at 200 minutes time on stream or at 300 minutes time on stream. The benzene productivity can be at least 0.5, or at least 0.6, or at least 0.8 kg benzene/((kg catalyst)–hour) at 50 minutes time on stream and can be at least 0.2, or at least 0.4, or at least 0.5, or at least 0.6 kg benzene/((kg catalyst)–hour) at 200 minutes time on stream or at 300 minutes time on stream. BTX productivity can be at least 0.9, or at least 1.0, or at least 1.4, or at least 1.6 kg of (benzene plus toluene plus xylene)/((kg catalyst)–hour)) at 50 minutes time on stream, and can be at least 0.8, or at least 1, or at least 1.2 kg of (benzene plus toluene plus xylene)/((kg catalyst)–hour) at 200 minutes time on stream or at 300 minutes time on stream. BTX productivity can be at least 0.2 or at least 0.4 (kg of benzene, toluene and xylene)/(kg catalyst)–hour at 300 minutes time on stream.

Thus, the feed stream comprising a lower hydrocarbon (e.g. a hydrocarbon having 2 to 4 carbon atoms) can be contacted with an aromatization catalyst at reaction conditions to convert the lower hydrocarbon to form an outlet stream comprising an aromatic hydrocarbon. The feed stream is introduced at a GHSV of greater than or equal to 4,000 ml·(g of Cat)$^{-1}$·h$^{-1}$, and a pressure of greater than or equal to 0.4 MPa. The feed stream can include hydrogen in an amount of at least 0.1 vol %, or at least 0.5 vol %, or at least 1 vol % up to 20 vol %, or up to 15 vol %, or up to 10 vol %, or up to 8 vol %, or up to 5 vol %, or up to 3 vol % based on total volume of the feed stream. For example, the feed stream can comprise hydrogen in amounts 0.1 to 20 vol %, or 0.1 to 15 vol %, or 0.1 to 10 vol %, or 0.1 to 8 vol %, or 0.1 to 5 vol %, or 0.1 to 3 vol %, or 0.5 to 20 vol %, or 0.5 to 15 vol %, or 0.5 to 10 vol %, or 0.5 to 8 vol %, or 0.5 to 5 vol %, or 0.5 to 3 vol %, or 1 to 20 vol %, or 1 to 15 vol %, 1 to 10 vol %, or 1 to 8 vol %, or 1 to 5 vol %, or 1 to 3 vol %.

The feed stream comprises one or more lower hydrocarbons. For example, the lower hydrocarbons can have two, three, or four carbon atoms. The feed stream can comprise one or more alkanes such as ethane, propane or butane. The feed stream may optionally include other hydrocarbons, particularly other lower hydrocarbons such as methane. The feed stream preferably comprises ethane. For example, the feed stream can comprise 0 to 5 mol % methane, 50-100, 75-100, 80-100 or 90-100 mole percent (mol %) of a hydrocarbon having two carbon atoms (e.g. ethane), 0 to 50 mol % of hydrocarbons having 3 or 4 carbon atoms (e.g. propane and/or butane). As another example, the feed stream can comprise (a) from at least 75, or at least 80, or at least 85, or at least 90, or at least 95 volume percent (vol %) ethane up to 100 vol % ethane; (b) 0% up to 5 vol % methane; (c) 0% up to 5 vol %, or 0 to 10 vol %, propane; and (d) 0% up to 5 vol %, or 0 to 10 vol %, butane. The feed stream can comprise from at least 75, or at least 80, or at least 85, or at least 90, or at least 95 vol % ethane up to 97, or up to 98.5, or up to 99, or up to 99.5, or up to 99.9 vol % ethane or, in the instance where the feed stream does not include hydrogen up to 100% ethane. (e.g. 75 to 100 vol %, 80 to 100 vol %, 85 to 100 vol %, 90 to 100 vol %, 95 to 100 vol %, 75 to 99.9 vol %, or 75 to 99 vol %, or 75 to 98.5 vol %, or 75 to 97 vol %, or 80 to 99.9 vol %, or 80 to 99 vol %, or 80 to 98.5 vol %, or 80 to 97 vol %, or 85 to 99.9 vol %, or 85 to 99 vol %, or 85 to 98.5 vol %, or 85 to 97 vol %, or 90 to 99.9 vol %, or 90 to 99 vol %, or 90 to 98.5 vol %, or 90 to 97 vol %, or 95 to 99.9 vol %, or 95 to 99 vol %, or 95 to 98.5 vol %, or 95 to 97 vol %). The feed stream may comprise 0% up to 5 vol % methane. The feed stream can comprise 0% up to 5 vol %, or up to 10 vol %, propane. For example, the feed stream can comprise 0 to 10 vol %, or 0 to 5 vol %, or 0.1 to 10 vol %, or 0.1 to 5 vol %, or 1 to 10 vol %, or 1 to 5 vol % propane. The feed stream may comprise 0% up to 5 vol %, or up to 10 vol %, butane. For example the feed stream can comprise 0 to 10 vol %, or 0 to 5 vol %, or 0.1 to 10 vol %, or 0.1 to 5 vol %, or 1 to 10 vol %, or 1 to 5 vol %, butane. For example, the feed stream can comprise 0.1 to 10 vol % hydrogen, 75 to 99.9 vol % ethane, 0 to 5 vol % methane, 0 to 10 vol % propane, and 0 to 10 vol % butane. Optionally, the only hydrogen that the catalyst is exposed to is in the feed stream.

The feed stream is introduced to the catalyst at a pressure of at least 0.4, or at least 0.5, MPa. The pressure of the feed stream can be up to 10, up to 9, up to 8, up to 7, up to 6, up to 5, up to 4, up to 3, up to 2, up to 1.5 or up to 1, MPa. For example, the pressure can be 0.4 to 10 MPa, or 0.4 to 9 MPa, or 0.4 to 8 MPa, or 0.4 to 7 MPa, or 0.4 to 6 MPa, or 0.4 to 5 MPa, or 0.4 to 4 MPa, or 0.4 to 3 MPa, or 0.4 to 2 MPa, or 0.4 to 1.5 MPa, or 0.4 to 1 MPa, or 0.5 to 10 MPa, or 0.5 to 9 MPa, or 0.5 to 8 MPa, or 0.5 to 7 MPa, or 0.5 to 6 MPa, or 0.5 to 5 MPa, or 0.5 to 4 MPa, or 0.5 to 3 MPa, or 0.5 to 2 MPa, or 0.5 to 1.5 MPa, or 0.5 to 1 MPa.

The feed stream is at a gas hourly velocity speed (GHSV) of at least 4,000, or at least 4,500, or at least 5,000, or at least 6,000, or at least 7,000, or at least 8,000, or at least 9,000 ml·(g of Cat)$^{-1}$·h$^{-1}$. GHSV can be up to 15,000, or up to 12,000, or up to 10,000, or up to 8000 ml·(g of Cat)$^{-1}$·h$^{-1}$. For example, the GHSV can be 4,000 to 15,000 ml·(g of Cat)$^{-1}$·h$^{-1}$, 4,000 to 12,000 ml·(g of Cat)$^{-1}$·h$^{-1}$, 4,000 to 10,000 ml·(g of Cat)$^{-1}$·h$^{-1}$, 4,000 to 8,000 ml·(g of Cat)$^{-1}$·h$^{-1}$, 5,000 to 15,000 ml·(g of Cat)$^{-1}$·h$^{-1}$, 5,000 to 12,000 ml·(g of Cat)$^{-1}$·h$^{-1}$, 5,000 to 10,000 ml·(g of Cat)$^{-1}$·h$^{-1}$, 5,000 to 8,000 ml·(g of Cat)$^{-1}$·h$^{-1}$, 6,000 to 15,000 ml·(g of Cat)$^{-1}$·h$^{-1}$, 6,000 to 12,000 ml·(g of Cat)$^{-1}$·h$^{-1}$, 6,000 to 10,000 ml·(g of Cat)$^{-1}$·h$^{-1}$, 6,000 to 8,000 ml·(g of Cat)$^{-1}$·h$^{-1}$. GHSV, as used herein, means the ratio of gas flow rate to the mass of the catalyst bed in the reactor.

The catalyst can be any known aromatization catalyst. For example, the catalyst can comprise one or more active metals deposited on an inorganic support. The catalyst optionally can further comprise promoters or other beneficial compounds.

Examples of such active metals include noble metals, group VIII metals, Gallium, Iron, Copper, Nickel, Tin, Rhenium, Germanium, and Iridium. For example, the active metal can comprise at least one of gallium, rhodium, and platinum. A single such active metal can be used or combinations of two or more can be used. For example, catalysts can include compounds of noble metals, compounds of group VII or VIII metals, which may be combined with zeolites. The inorganic support can be an inorganic oxide such as, for example, a silicate or an alumina silicate. The inorganic support can be a zeolite, such as ZSM-5, ZSM-8, ZSM-11, ZSM-12, or ZSM-35. The catalyst can comprise ZSM-5 with a silica to alumina ratio in the range of 23:1 to 100:1.

For example, the catalyst composition can comprise an aluminosilicate having gallium deposited thereon and/or an aluminosilicate in which cations have been exchanged with gallium ions. The molar ratio of silica to alumina can be at least 5:1 or at least 10:1 or at least 15:1. The molar ratio can be up to 40:1 or up to 35:1.

As another example, the catalyst can comprise a group VIII metal such as rhodium or platinum combined with an aluminosilicate. Gallium can also be used in combinations with the rhodium or platinum.

As another example, the catalyst may comprise a noble metal of the platinum family to promote the dehydrogenation reaction, and a second inert or less active metal which will attenuate the tendency of the noble metal to catalyze hydrogenolysis of the hydrocarbons in the feed which have two or more carbon atoms to methane. Attenuating metals which can be used include those described below.

As another example, the catalyst comprises an MFI zeolite plus at least one noble metal from the platinum family and at least one additional metal chosen from the group consisting of tin, germanium, lead, and indium.

One example of preparing a catalyst would be to provide a zeolite such as ZSM-5 and aluminum oxide ($Al_2O_3$) in desired amounts. For example, the amount of zeolite (e.g. ZSM-5) can be 75 to 95 weight percent (wt %), 80 to 90 wt %, or 85 wt %, based on total weight of zeolite and aluminum oxide. The amount of aluminum oxide can be 5 to 25 wt %, 10 to 20 wt %, or 15 wt %, based on total weight of zeolite and aluminum oxide. The zeolite and aluminum oxide can be calcined—e.g. a temperature above 600° C., such as at a temperature of 610° C. to 650° C. (e.g., 630° C.) for a period of time, such as 6 to 10 hours, e.g., 8 hours. Metal loading can be done by incipient wetness impregnation. The desired amount of metal precursor (e.g. Pt containing precursor, or Ga containing precursor) can be dissolved in water and impregnated onto the zeolite/aluminum oxide structure. The amount of water can be based upon pore volume of the zeolite/aluminum oxide calcined structure.

The catalyst can comprise from 10 to 99.9 wt % of one or more aluminosilicate materials, preferably from 30 to 99.9 wt %, based upon total weight of the catalyst. The aluminosilicates preferably have a silicon dioxide:aluminum trioxide ($SiO_2$:$Al_2O_3$) molar ratio of from 20 to 80. The aluminosilicates may preferably be zeolites having the MFI or MEL type structure and may be ZSM-5, ZSM-8, ZSM-11, ZSM-12 or ZSM-35. The zeolite or zeolite mixture is preferably converted to ft form (e.g., HZ SM-5) to provide sufficient acidity to help catalyze the dehydroaromatization reaction. This can be accomplished by calcining the ammonium form of the zeolite in air at a temperature of at least 400° C.

The final shaped catalyst could be in the form of cylindrical pellets, rings or spheres.

The catalyst is provided in a fixed bed reactor system.

The conversion of the lower hydrocarbon to aromatic hydrocarbon can occur at a temperature of at least 500° C., or at least 550° C. The conversion can occur at a temperature of no more than 700° C., or no more than 650° C. For example, the temperature for conversion can be 500-700, 500-650, 550-700 or 550-650° C.

Optionally, the process can exclude a step of contacting the catalyst with a stream comprising hydrogen other than the hydrogen in the feed stream.

The conversion generates aromatic compounds. Thus, the outlet stream comprises at least one aromatic compounds selected from benzene, toluene, and xylene.

The "conversion percentage" of the lower hydrocarbon feed stream is defined as 100 times (ethane in the feed stream minus the ethane exiting the reactor) divided by (ethane in the feed stream). Ethane concentration in input and output can be measured, for example, based on calibrated gas chromatography.

The "time on stream" means the total time for which catalyst was exposed to reaction conditions in presence of feed.

The "benzene productivity" mean kilograms of benzene produced per kilogram of catalyst per hour (kg/((kg of Cat)·h) or kg Bz–(kg of Cat)$^{-1}$·h$^{-1}$.

The "BTX productivity" means kilograms of benzene plus toluene plus xylenes produced per kilogram of catalyst per hour (kg/((kg of cat)·h) or kg BTX–(kg of Cat)$^{-1}$·h$^{-1}$.

This disclosure is further illustrated by the following examples, which are non-limiting.

EXAMPLES

Example 1

Ethane to benzene/aromatics experiments are carried out in a fixed bed reactor. A catalyst having 0.024 wt % Pt and 0.15 wt % Ga on a HZSM-5 zeolite with 15 wt % alumina binder was used with all percents being based on total weight of the catalyst. The catalyst bed temperature was measured using thermocouple. After loading, the catalyst was activated/reduced under hydrogen gas ($H_2$) at 600° C. and 1 bar or 5 bar (0.1 or 0.5 megaPascal (MPa) for 1 hour (h). The catalyst was then heated up to reaction temperature of 630° C. in the presence of nitrogen gas (N2) flow. Once the reaction temperature was reached, N2 flow was stopped and ethane feed was started at 0.1 MPa or 0.5 MPa and a gas hourly space velocity (GHSV) of 1,000 ml·(g of Cat)$^{-1}$·h$^{-1}$ (comparative) and at 5,000 ml·(g of Cat)$^{-1}$·h$^{-1}$, to initiate catalytic ethane aromatization reaction. To maintain required GHSV, ethane flow was adjusted based on catalyst weight. The reactor outlet composition was analyzed using an online gas chromatograph (GC).

Example 2

Figure 1B:
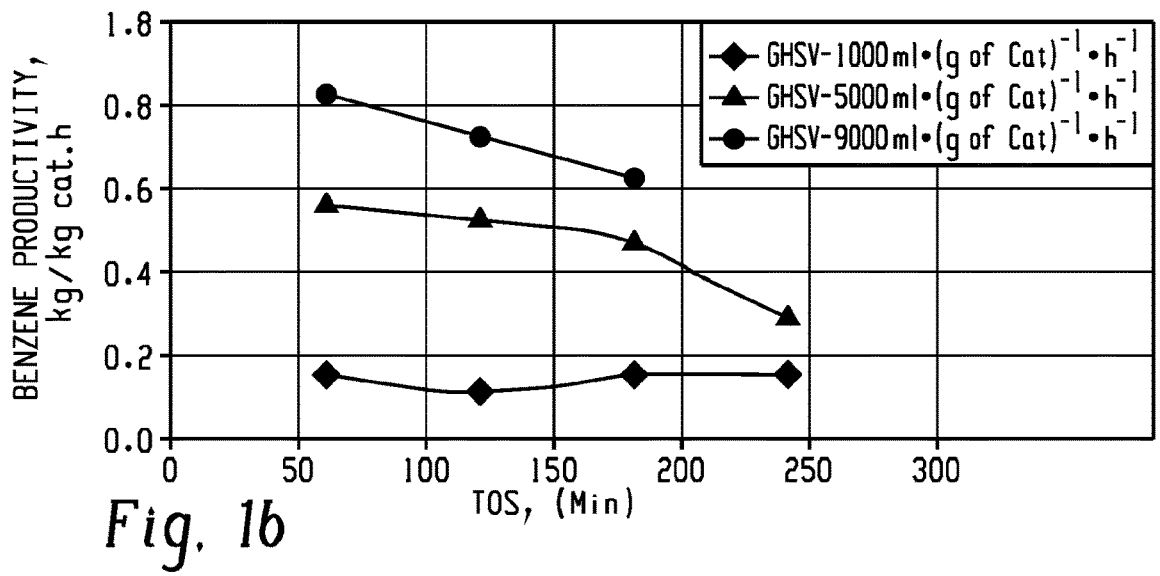
Figure 1C:
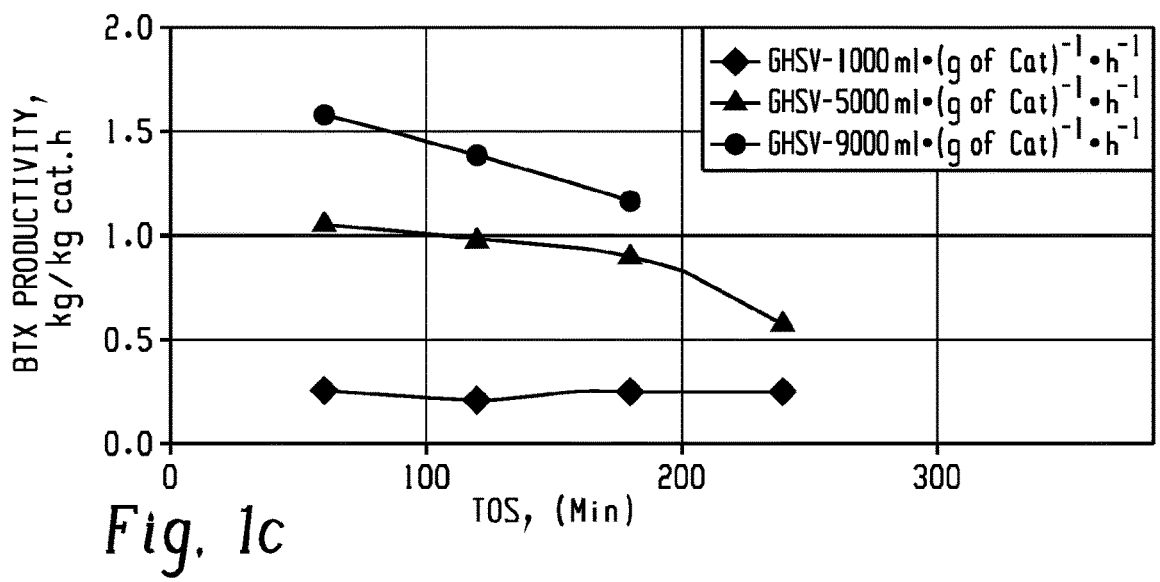

Tests were run substantially as set forth in Example 1 at a pressure of 5 bar (0.5 MPa) while varying GHSV at 1,000 (comparative), 5,000 and 9,000 ml·(g of Cat)$^{-1}$·h$^{-1}$. As shown in FIGS. 1a-1c, while ethane conversion is high at GHSV of 1,000 ml·(g of Cat)$^{-1}$·h$^{-1}$ (FIG. 1a), the ethane is not being converted to the desired aromatics as is shown in FIGS. 1b and 1c. Thus, a combination of high pressure (e.g. 0.5 MPa) and high GHSV (e.g. 5,000 or 9,000 ml·(g of Cat)$^{-1}$·h$^{-1}$) provides good conversion from lower hydrocarbon to aromatics.

Example 3

Figure 2A:
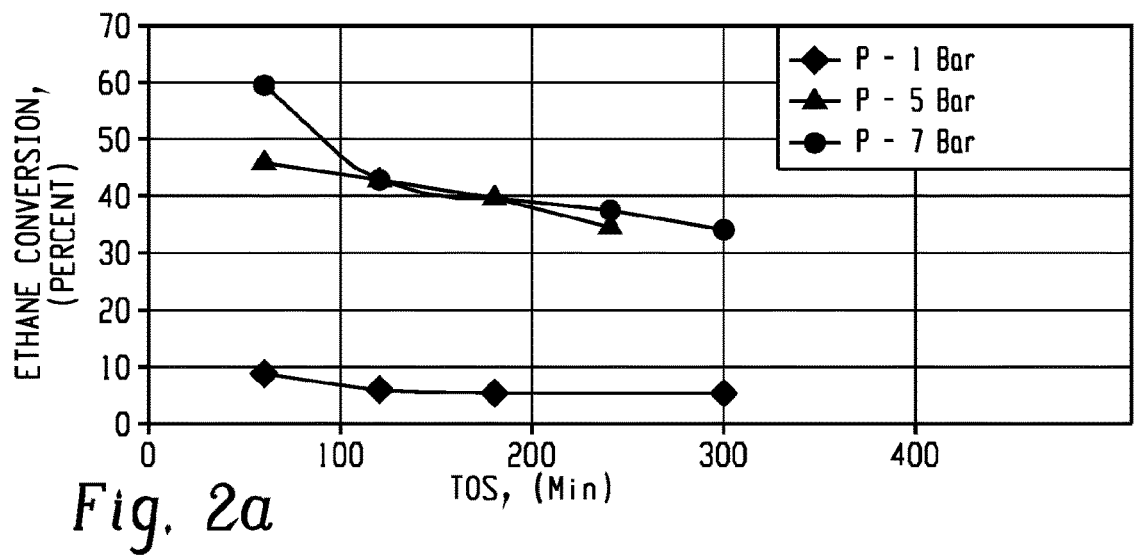
FIG. 2a-2c are graphical representations of ethane conversion, benzene productivity and BTX productivity for a variety of pressures at GHSV of 5000 ml·(g of Cat)$^{-1}$·h$^{-1}$.
Figure 2B:
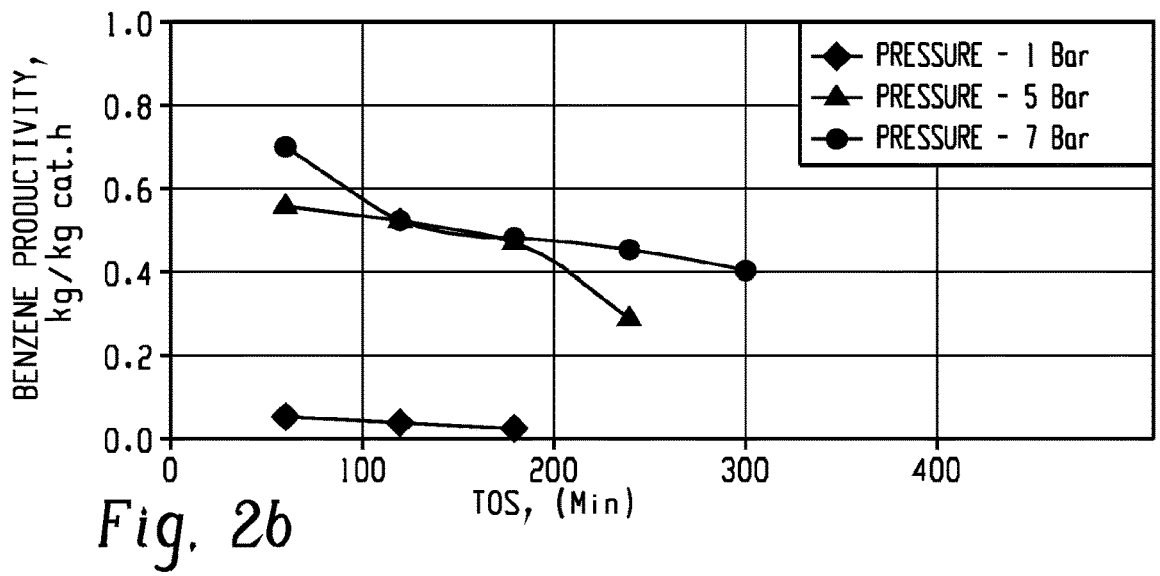
Figure 2C:
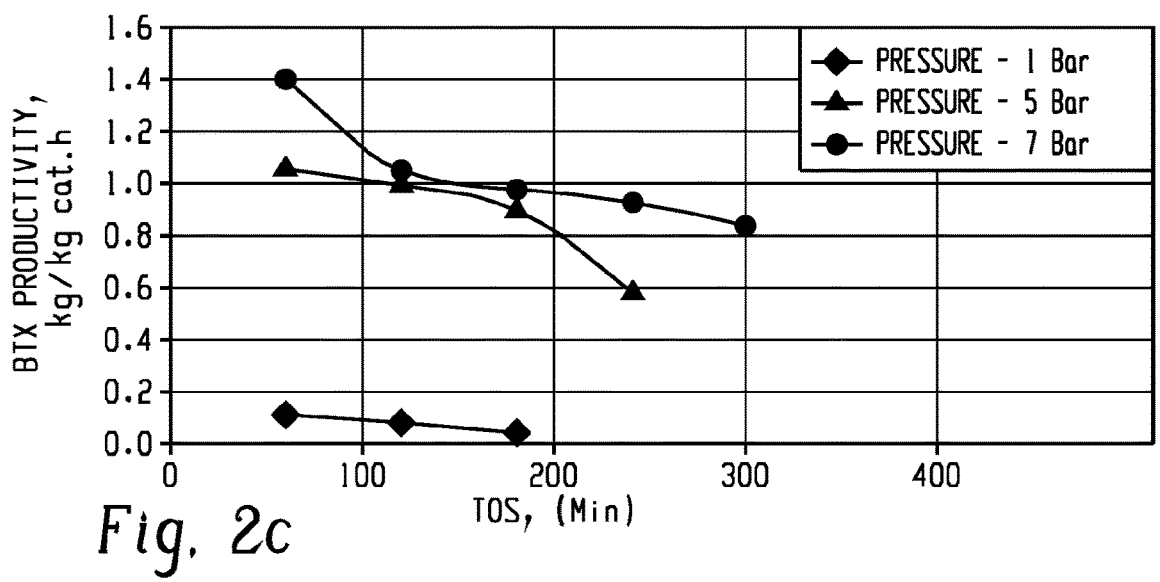

Tests were run substantially as set forth in Example 1 at a GHSV of 5,000 ml·(g of Cat)$^{-1}$·h$^{-1}$ and pressures of 1 (comparative), 5, and 7 bar (0.1, 0.5 and 0.7 MPa). As can be seen from FIGS. 2a-2c, at the 5000 ml·(g of Cat)$^{-1}$·h$^{-1}$ GHSV, and the higher pressures (e.g. 0.5 or 0.7 MPa) yields better ethane conversion and aromatics productivity.

The Examples 1-3 reveal a surprising improvement in ethane conversion to aromatics when a combination of pressure of greater than or equal to 0.4 MPa (e.g., 0.5 MPa or 0.7 MPa) is used in combination with a GHSV of greater or equal to 4000 ml·(g of Cat)$^{-1}$·h$^{-1}$ (e.g. 5000 or 9000 ml·(g of Cat)$^{-1}$·h$^{-1}$).

Example 4—Effect of Hydrogen on Ethane Conversion, and Aromatic Productivity at High Pressure and Flow Rate Ethane to benzene/aromatics conversion experiments are carried out in a fixed bed reactor. Pt-Ga/ZSM-5 based catalyst, in the form of extrudate (with $Al_2O_3$ binder), is used for all laboratory experiments. The catalyst composition was 0.024 wt % Pt and 0.15 wt % Ga on HZSM-5 zeolite with 15% alumina binder. (The catalyst can be prepared by calcining at 630° C. for 8 hours ZSM-5 and SCF55 (alumina binder precursor. Then the metal precursor are dissolved in desired amounts in water and impregnated onto the zeolite.

All weight percents are based on total weight of the catalyst). The catalyst bed temperature was measured using thermocouple. After loading, the catalyst was activated/reduced under $H_2$ at 600° C. and 0.5 megaPascal (MPa) for 1 hour (h). The catalyst was then heated up to reaction temperature of 630° C. in the presence of N2 flow. Once the reaction temperature was reached, N2 flow was stopped and ethane feed was started at 0.5 MPa and a gas hourly space velocity (GHSV) of 5,000 ml·(g of Cat)$^{-1}$·h$^{-1}$ to initiate catalytic ethane aromatization reaction in the fixed bed reactor. The reactor outlet composition was analyzed using an online gas chromatograph (GC).

In order to know the effect of hydrogen co-feed on long-term ethane aromatization catalyst stability, experiments are performed at 630° C., GHSV of 5,000 ml·(g of Cat)$^{-1}$·h$^{-1}$ and 0.5 MPa using $H_2$ concentrations of 0, 1.6, 6, 12 and 20 vol %. Five different responses are used to measure catalyst performance and stability: ethane conversion, benzene productivity, BTX productivity, heavies (i.e. compounds with nine or more carbon atoms, i.e. $C^{9+}$) productivity and methane productivity.

Figure 3:
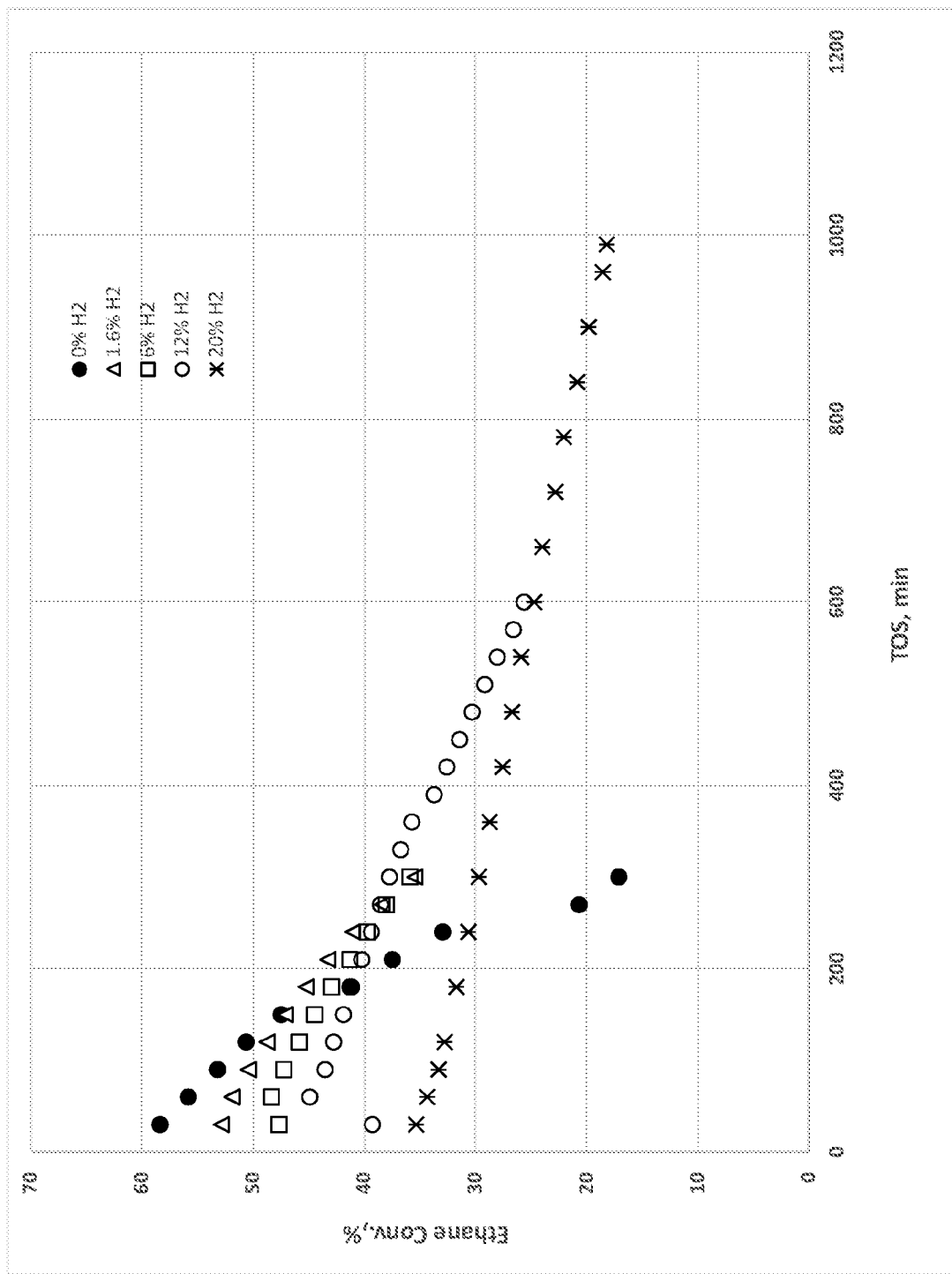
FIG. 3 is a graphical representation of ethane conversion percentage versus time on stream (TOS) in minutes (min) for a feed stream at 0.5 MPa and a gas hourly space velocity (GHSV) of 5,000 ml·(g of Cat)$^{-1}$·h$^{-1}$ with varying amounts of hydrogen in the feed stream.

As shown in FIG. 3, the presence of small amount of $H_2$ remarkably extends the higher rates of ethane conversion for a longer TOS. After about 5 hours of continuous reaction, approximately 70% decrease in ethane conversion is observed in the absence of $H_2$. In contrast, in the presence of $H_2$, the decrease in ethane conversion at 5 hours is found to be significantly smaller. Low amounts of $H_2$ show comparably initial performance to samples run without hydrogen.

Figure 4:
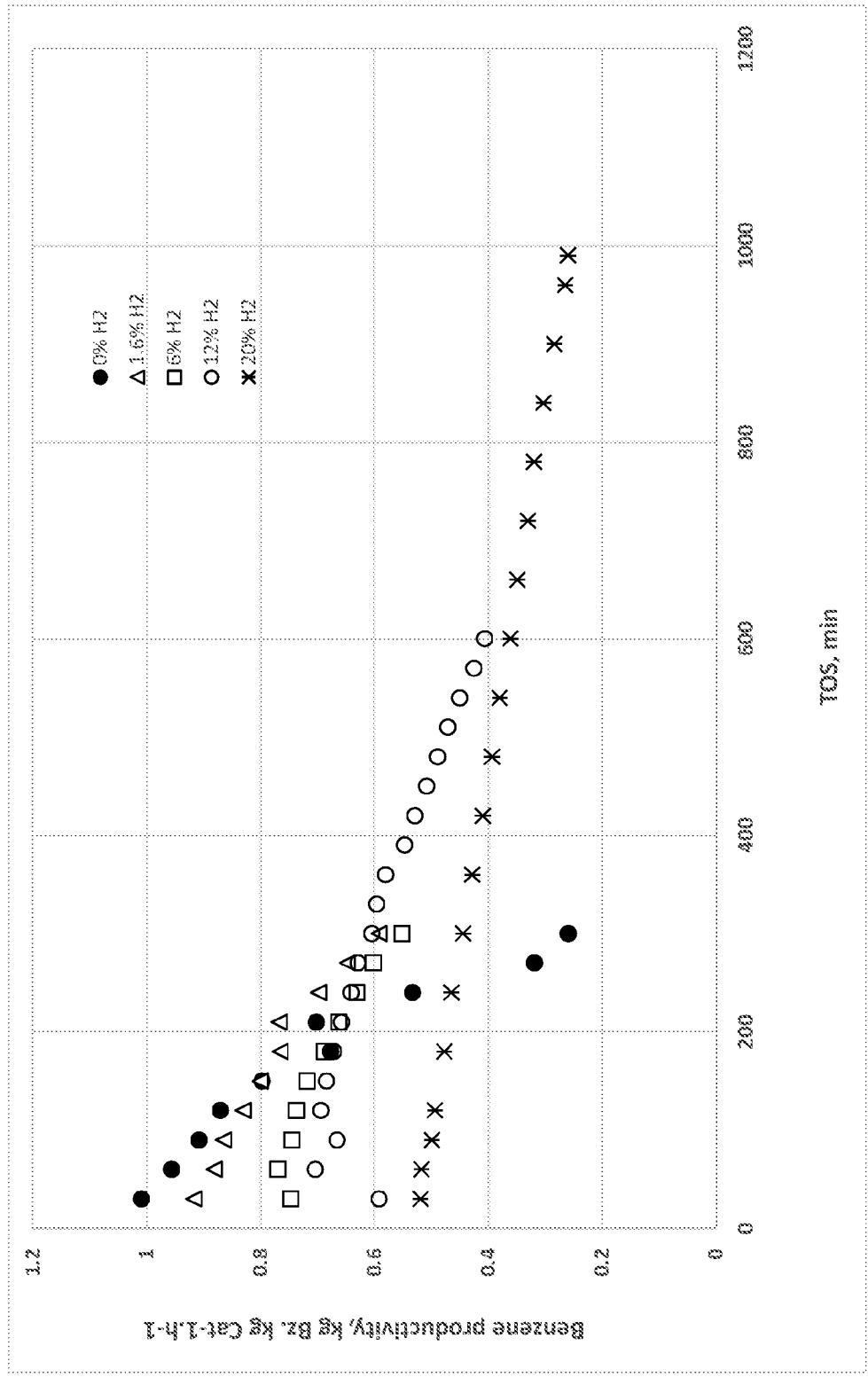
FIG. 4 is a graphical representation of benzene productivity versus TOS at 0.5 MPa and a gas hourly space velocity (GHSV) of 5,000 ml·(g of Cat)$^{-1}$·h$^{-1}$ with varying amounts of hydrogen in the feed stream.
Figure 5:
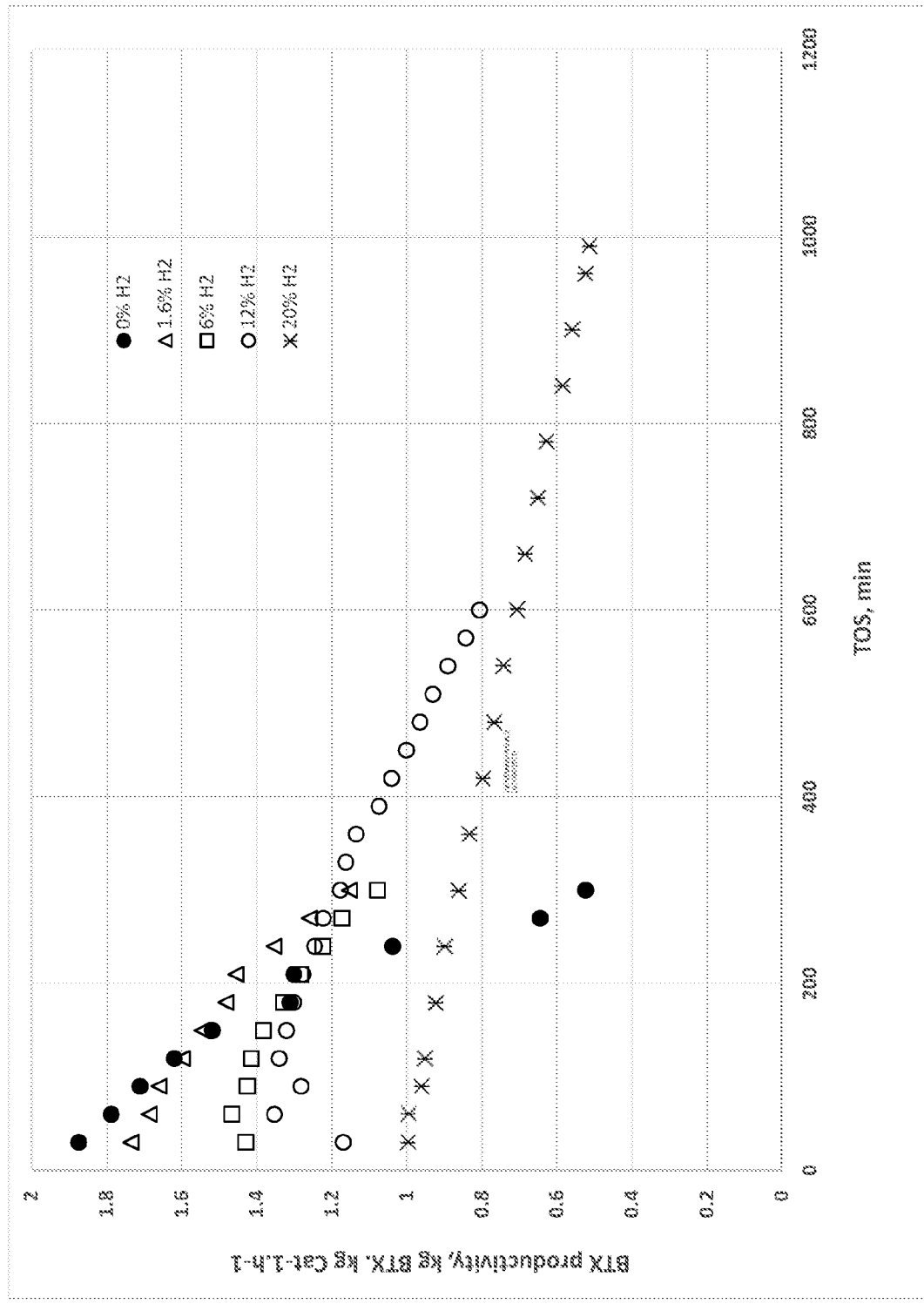
FIG. 5 is a graphical representation of benzene, toluene, xylene (BTX) productivity versus TOS at 0.5 MPa and a gas hourly space velocity (GHSV) of 5,000 ml·(g of Cat)$^{-1}$·h$^{-1}$ with varying amounts of hydrogen in the feed stream.

A similar effect of $H_2$ on benzene as well as benzene, toluene, xylene (BTX) productivity was observed, as is illustrated in FIGS. 4 and 5. The benzene and BTX productivities, after about 5 hours of reaction, in the presence of $H_2$ are significantly higher (in several instances over twice as high) as compared to the productivities at 5 hours in the absence of $H_2$. Low amounts of $H_2$ show comparable initial performance to samples run without hydrogen.

Above results clearly indicate that, feed streams at high pressure and GHSV and small amounts of hydrogen, good ethane conversion and aromatic productivity can be achieved while extending the long-term performance of the catalyst.

Figure 6:
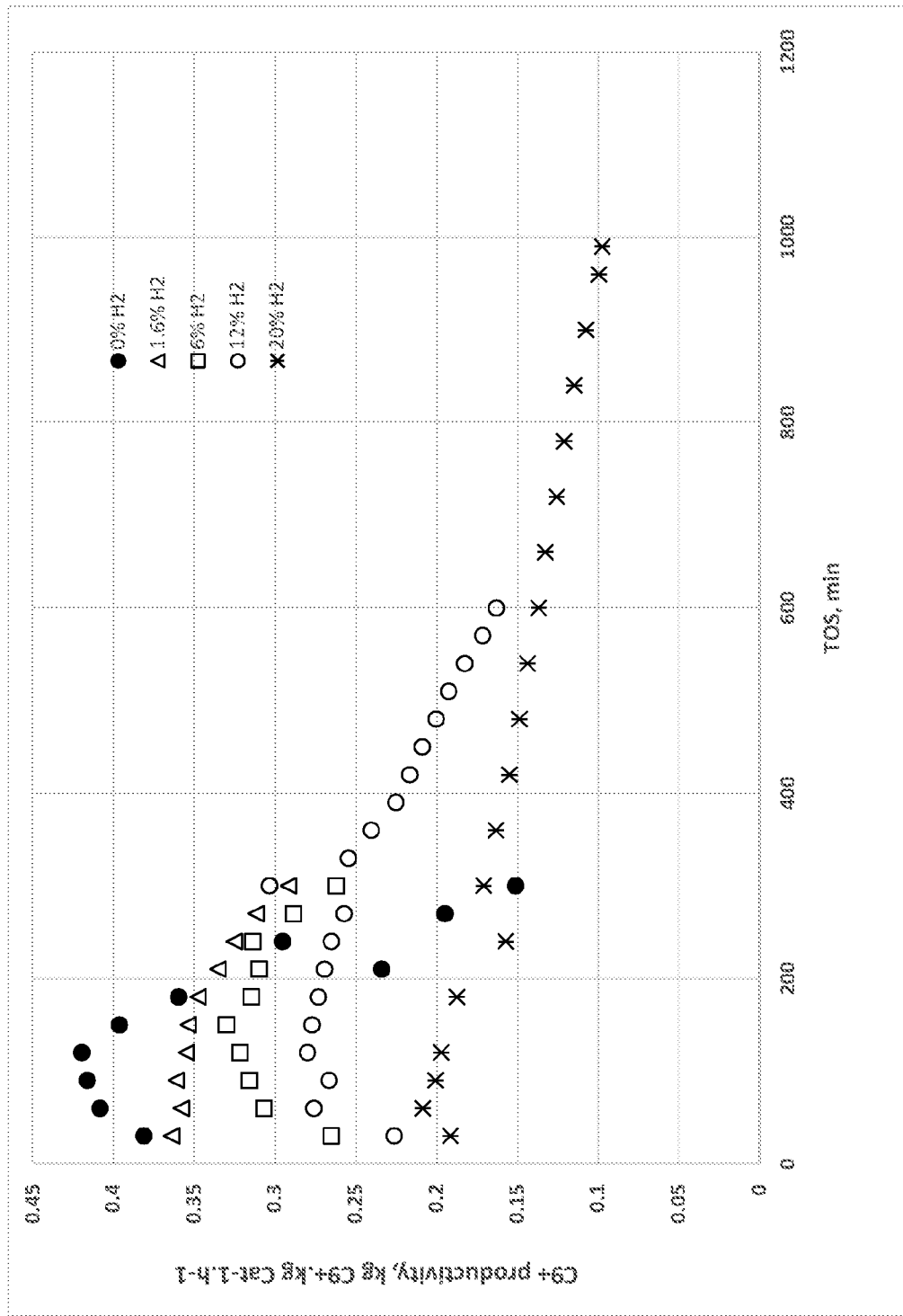
FIG. 6 is a graphical representation of $C^{9+}$ productivity versus TOS at 0.5 MPa and a gas hourly space velocity (GHSV) of 5,000 ml·(g of Cat)$^{-1}$·h$^{-1}$ with varying amounts of hydrogen in the feed stream.

Additionally, FIG. 6, shows the heavies (i.e., $C^{9+}$ aromatics) formation in kilograms of $C^{9+}$ aromatics per kilogram of catalyst per hour (kg $C^{9+}$·kg Cat$^{-1}$·h$^{-1}$) with and without the presence of $H_2$.

Figure 7:
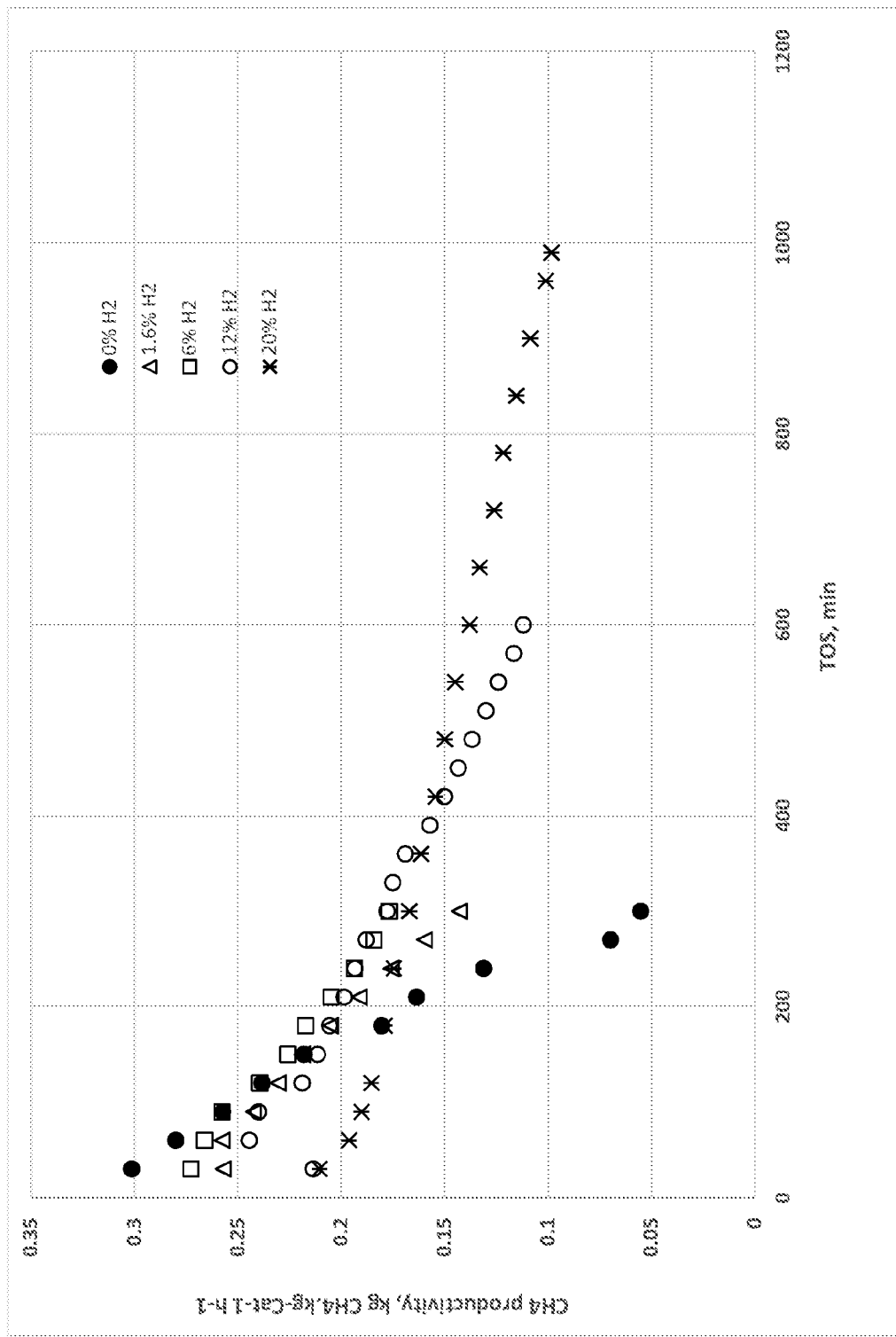
FIG. 7 is a graphical representation of methane productivity versus TOS at 0.5 MPa and a gas hourly space velocity (GHSV) of 5,000 ml·(g of Cat)$^{-1}$·h$^{-1}$ with varying amounts of hydrogen in the feed stream.

FIG. 7 shows methane ($CH_4$) formation ($CH_4$·kg Cat$^{-1}$·h$^{-1}$) with and without the presence of $H_2$. Up to about 3 hours methane is lower in the products with 1.6% $H_2$ as co-feed compared to 0% $H_2$. However, in the later stage of the reaction there is marginal increase in methane with 1.6% $H_2$ co-feed due to higher ethane conversion as compared to the reaction with 0% $H_2$ co-feed.

The above findings show that the small amount of $H_2$ in the feed is beneficial for ethane aromatization. It helps significantly in improving long-term catalyst performance, e.g., possibly through reducing naphthalene/coke precursor formation and/or facilitating decoking.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "a" and "an" and "the" do not denote a limitation of quantity and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments. A "combination thereof" is open and includes any combination comprising at least one of the listed components or properties optionally together with a like or equivalent component or property not listed.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

This disclosure further encompasses the following aspects.

Aspect 1: A method for the aromatization of hydrocarbons, comprising: introducing a feed stream to an aromatization catalyst in a fixed bed reactor wherein the feed stream comprises the one or more hydrocarbons having 2 to 4 carbon atoms, converting the one or more hydrocarbons to form an outlet stream comprising an aromatic hydrocarbon; wherein the feed stream is introduced at a GHSV of greater than or equal to 4,000 ml·(g of Cat)$^{-1}$·h$^{-1}$, and a pressure of greater than or equal to 0.4 MPa.

Aspect 2: The method of Aspect 1, wherein the one or more hydrocarbons comprises ethane.

Aspect 3: The method of aspect 1 or 2 wherein the one or more hydrocarbons comprises 0 to 5 mole percent methane, 90-100 mole percent ethane, and 0 to 5 mole percent hydrocarbons of 3 or 4 carbon atoms.

Aspect 4: The method of any of the preceding aspects, wherein the GHSV is 4,000 ml·(g of Cat)$^{-1}$·h$^{-1}$ to 10,000 ml·(g of Cat)$^{-1}$·h$^{-1}$, preferably 5,000 ml·(g of Cat)$^{-1}$·h$^{-1}$ to 10,000 ml·(g of Cat)$^{-1}$·h$^{-1}$, more preferably greater than 6000 ml·(g of Cat)$^{-1}$·h$^{-1}$ to 10,000 ml·(g of Cat)$^{-1}$·h$^{-1}$.

Aspect 5: The method of any of the preceding aspects, wherein the GHSV is greater than 4000, preferably 5000, more preferably 6000 ml·(g of Cat)$^{-1}$·h$^{-1}$.

Aspect 6: The method of any of the preceding aspects, wherein the pressure is 0.4 MPa to 10 MPa, preferably 0.5 MPa to 8 MPa, more preferably 0.6 to 5 MPa.

Aspect 7: The method of any of the preceding aspects, wherein the converting occurs at a temperature in the range of 500 to 700° C.

Aspect 8: The method of any of the preceding aspects, wherein the feed stream consists essentially of ethane.

Aspect 9: The method of any of the preceding aspects wherein the feed stream comprises less than 1, preferably less than 0.75, weight percent carbon dioxide, preferably the feed stream is free of carbon dioxide.

Aspect 10: The method of any of the preceding aspects wherein the feed comprises less than 0.75, preferably less than 0.5, volume percent carbon monoxide, preferably the feed stream is free of carbon monoxide.

Aspect 11: The method of any of the preceding aspects wherein the ethane conversion is at least 30%, preferably at least 50% at 50 minutes time on stream and at least 20% at 200 minutes time on stream.

Aspect 12: The method of any of the preceding aspects wherein the benzene conversion is at least 0.5 kg/(kg catalyst)–hour at 50 minutes time on stream and/or at least 0.4 kg/(kg catalyst)–hour at 200 minutes time on stream.

Aspect 13: The method of any of the preceding aspects wherein BTX productivity is at least 1, preferably at least 1.4, (kg of benzene plus toluene plus xylene)/(kg catalyst)–hour at 50 minutes time on stream and/or is be at least 0.8 preferably at least kg of benzene plus toluene plus xylene)/ (kg catalyst)–hour at 200 minutes time on stream Aspect 14: The method of any of the preceding aspects wherein the feed stream further comprises hydrogen in an amount of at least 0.1 vol %, preferably at least 0.5 vol %, more preferably at least 1.0 vol % up to 20 vol %, preferably up to 10 vol %, more preferably up to 5 vol %, yet more preferably up to 3 vol % based upon total volume of the feed stream.

Aspect 15. A method for the aromatization of hydrocarbon, comprising: introducing to a fixed bed reactor containing an aromatization catalyst a feed stream comprising hydrocarbon having 2 to 4 carbon atoms and hydrogen, wherein the amount of hydrogen is at least 0.1 vol %, preferably at least 0.5 vol %, more preferably at least 1.0 vol % up to 20 vol %, preferably up to 10 vol %, more preferably up to 5 vol %, yet more preferably up to 3 vol % based upon total volume of the feed stream; converting the hydrocarbon having 2 to 4 carbon atoms to form an outlet stream comprising an aromatic hydrocarbon; wherein the feed stream is introduced at a GHSV of greater than or equal to 4,000 ml·(g of Cat)$^{-1}$·h$^{-1}$, and a pressure of greater than or equal to 0.4 MPa.

Aspect 16. The method of Aspect 15, wherein the feed stream comprises ethane.

Aspect 17. The method of any of Aspects 15-16, wherein the GHSV is 4,000 ml·(g of Cat)$^{-1}$·h$^{-1}$ to 10,000 ml·(g of Cat)$^{-1}$·h$^{-1}$, preferably 5,000 ml·(g of Cat)$^{-1}$·h$^{-1}$ to 10,000 ml·(g of Cat)$^{-1}$·h$^{-1}$.

Aspect 18. The method of any of Aspects 15-17, wherein the pressure is 0.4 MPa to 10 MPa, preferably 0.5 MPa to 8 MPa.

Aspect 19. The method of any of Aspects 15-18, wherein the hydrogen is present in the feed stream in an amount of 1.5 vol % to 2.5 vol %.

Aspect 20. The method of any of Aspects 15-19, wherein the feed stream comprises 0.1 to 10 vol % hydrogen, 75 to 99.9 vol % ethane, 0 to 5 vol % methane, 0 to 10 vol % propane, and 0 to 10 vol % butane.

Aspect 21. The method of any of Aspects 15-20, wherein the converting occurs at a temperature in the range of 500 to 700° C.

Aspect 22. The method of any of Aspects 15-21, wherein the feed stream comprises 75 to 99.9 vol % ethane.

Aspect 23. The method of any of Aspects 15-22 which does not include a step of contacting the catalyst with a stream comprising hydrogen other than the hydrogen in the feed stream.

Aspect 24. The method of any of Aspects 15-23, wherein the only hydrogen that the catalyst is exposed to is in the feed stream.

Aspect 25. The method any of Aspects 15-23 consisting essentially of, preferably consisting of, introducing to a fixed bed reactor containing an aromatization catalyst a feed stream comprising hydrocarbon having 2 to 4 carbon atoms and hydrogen, wherein the amount of hydrogen is at least 0.1 vol %, preferably at least 0.5 vol %, more preferably at least 1.0 vol % up to 20 vol %, preferably up to 10 vol %, more preferably up to 5 vol %, yet more preferably up to 3 vol % based upon total volume of the feed stream; converting the hydrocarbon having 2 to 4 carbon atoms to form an outlet stream comprising an aromatic hydrocarbon; wherein the feed stream is introduced at a GHSV of greater than or equal to 4,000 ml·(g of Cat)$^{-1}$·h$^{-1}$, and a pressure of greater than or equal to 0.4 MPa.

What is claimed is:

1. A method for the aromatization of hydrocarbons, comprising:
    introducing a feed stream to an aromatization catalyst in a fixed bed reactor wherein the feed stream comprises a hydrocarbon having 2 to 4 carbon atoms,
    converting the hydrocarbon having 2 to 4 carbon atoms to form an outlet stream comprising an aromatic hydrocarbon;
    wherein the feed stream is introduced at a GHSV of greater than or equal to 4,000 ml·(g of Cat)$^{-1}$·h$^{-1}$, and a pressure of greater than or equal to 0.4 MPa, wherein the method does not include contacting the catalyst with a stream comprising hydrogen other than hydrogen in the feed stream.

2. The method of claim 1, wherein the feed stream comprises ethane.

3. The method of claim 1 wherein the feed stream comprises 0 to 5 mole percent methane, 90-100 mole percent ethane, and 0 to 5 mole percent hydrocarbons having 3 or 4 carbon atoms based on total moles of hydrocarbons in the feed stream.

4. The method of claim 1 wherein the GHSV is 4,000 ml·(g of Cat)$^{-1}$·h$^{-1}$ to 10,000 ml·(g of Cat)$^{-1}$·h$^{-1}$.

5. The method of claim 3 wherein the GHSV is 5,000 ml·(g of Cat)$^{-1}$·h$^{-1}$ to 10,000 ml·(g of Cat)$^{-1}$·h$^{-1}$.

6. The method of claim 3 wherein the GHSV is 6000 ml·(g of Cat)$^{-1}$·h$^{-1}$ to 10,000 ml·(g of Cat)$^{-1}$·h$^{-1}$.

7. The method of claim 1, wherein the pressure is 0.4 MPa to 10 MPa.

8. The method of claim 6 wherein the pressure is 0.5 MPa to 8 MPa.

9. The method of claim 1 wherein the converting occurs at a temperature in the range of 500 to 700° C.

10. The method of claim 1 wherein the feed stream comprises less than 1 weight percent carbon dioxide.

11. The method of claim 1 wherein the feed stream comprises less than 1 volume percent carbon monoxide.

12. The method of claim 1 wherein the feed stream comprises hydrogen in an amount of at least 0.1 vol % up to 20 vol %, based upon total volume of the feed stream.

13. The method of claim 1 wherein the feed stream comprises 0.1 to 10 vol % hydrogen, 75 to 99.9 vol % ethane, 0 to 5 vol % methane, 0 to 10 vol % propane, and 0 to 10 vol % butane.

14. The method of claim 1 consisting essentially of introducing to a fixed bed reactor containing an aromatization catalyst a feed stream comprising hydrocarbon having 2 to 4 carbon atoms and hydrogen, wherein the amount of hydrogen is 0-20 vol %, based upon total volume of the feed stream; converting the hydrocarbon having 2 to 4 carbon atoms to form an outlet stream comprising an aromatic hydrocarbon; wherein the feed stream is introduced at a GHSV of greater than or equal to 4,000 ml·(g of Cat)$^{-1}$·h$^{-1}$, and a pressure of greater than or equal to 0.4 MPa.

15. The method of claim 12, wherein the only hydrogen that the catalyst is exposed to is in the feed stream.

16. A method for the aromatization of hydrocarbons, comprising:

introducing a feed stream to an aromatization catalyst in a fixed bed reactor wherein the feed stream comprises a hydrocarbon having 2 to 4 carbon atoms, converting the hydrocarbon having 2 to 4 carbon atoms to form an outlet stream comprising an aromatic hydrocarbon;

wherein the feed stream is introduced at a GHSV of greater than or equal to 4,000 ml·(g of Cat)$^{-1}$·h$^{-1}$, and a pressure of greater than or equal to 0.4 MPa, wherein the converting continues for at least 50 minutes time on stream.

17. The method of claim 16 wherein the feed stream comprises hydrogen in an amount of at least 0.1 up to 20 vol % based upon total volume of the feed stream.

18. The method of claim 16 wherein the feed stream comprises 50 to 100 mole % ethane based on total hydrocarbons in the feed stream.

19. The method of claim 17 wherein at least 0.5 kilograms benzene/kilogram catalyst-hour are produced at 300 minutes time on stream.

20. The method of claim 16 wherein at least 0.5 kilograms benzene/kilogram catalyst-hour are produced at 50 minutes time on stream.

* * * * *